United States Patent [19]
Enscore et al.

[11] Patent Number: 5,342,623
[45] Date of Patent: * Aug. 30, 1994

[54] SUBSATURATED TRANSDERMAL THERAPEUTIC SYSTEM HAVING IMPROVED RELEASE CHARACTERISTICS

[75] Inventors: David J. Enscore, Sunnyvale; Patricia S. Campbell, Palo Alto; James L. Osborne, Mountain View; Melinda K. Smart, Sunnyvale; Su I. Yum, Los Altos, all of Calif.

[73] Assignee: ALZA Corporation, Palo Alto, Calif.

[*] Notice: The portion of the term of this patent subsequent to Apr. 2, 2008 has been disclaimed.

[21] Appl. No.: 80,645

[22] Filed: Jun. 18, 1993

Related U.S. Application Data

[63] Continuation of Ser. No. 284,283, Dec. 14, 1988, abandoned, which is a continuation-in-part of Ser. No. 906,730, Sep. 12, 1986, Pat. No. 4,908,027.

[51] Int. Cl.⁵ ............................................. A61F 13/02
[52] U.S. Cl. .................................. 424/448; 424/447; 424/449
[58] Field of Search .................. 424/448, 447, 449

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,731,683 | 5/1973 | Zaffaroni | 604/304 |
| 3,734,097 | 5/1973 | Zaffaroni | 604/304 |
| 3,742,951 | 7/1973 | Zaffaroni | 128/268 |
| 3,923,939 | 12/1975 | Baker et al. | 264/49 |
| 3,926,188 | 12/1975 | Baker et al. | 424/427 |

(List continued on next page.)

FOREIGN PATENT DOCUMENTS

| | | |
|---|---|---|
| 0117027 | 8/1984 | European Pat. Off. |
| 860152 | 3/1985 | Fed. Rep. of Germany |
| 3438284 | 3/1985 | Fed. Rep. of Germany |
| 2171906 | 9/1986 | United Kingdom |

OTHER PUBLICATIONS

Baker, R. W., et al., "Controlled Release: Mechanisms and Rates," Advanced Experimental Med. Biol., vol. 47, pp. 15–71 (1974).
The Merck Index, Ninth Edition, pp. 117 and 160, Published by Merck & Company, Inc., (1976).

Primary Examiner—D. Gabrielle Phelan
Attorney, Agent, or Firm—Steven F. Stone; Paul L. Sabatine; Edward L. Mandell

[57] ABSTRACT

Rate controlled transdermal delivery devices are disclosed which utilize an in-line adhesive to maintain the device on the skin and deliver an agent which is a solvent or a plasticizer for the in-line adhesive. The initial equilibrated concentration of the agent in the agent reservoir and the adhesive is below saturation, and the reservoir comprises the agent dissolved in a solvent with respect to which the rate controlling element of the device is substantially impermeable. In preferred embodiments the initial loading of the agent in reservoir is sufficient to prevent the activity of the agent in the reservoir from decreasing by more than about 50% and preferably no more than about 25% during the predetermined period of administration; and the thicknesses of the adhesive, rate controlling membrane and reservoir layers are selected so that at least 50% and preferably at least 75% initial equilibrated agent loading is in the reservoir layer. The devices are usable to deliver agents which are liquid at body temperatures such as benztropine, secoverine, nicotine, arecoline, polyethylene glycol monolaurate, glycerol monolaurate, glycerol monooleate and ethanol, for example.

15 Claims, 5 Drawing Sheets

U.S. PATENT DOCUMENTS

| | | | |
|---|---|---|---|
| 3,996,245 | 12/1976 | Hartog et al. | 549/451 |
| 3,996,934 | 12/1976 | Zaffaroni | 424/448 X |
| 4,031,894 | 6/1977 | Urquhart et al. | 128/268 |
| 4,060,084 | 11/1977 | Chandrasekaran et al. | 128/260 |
| 4,125,623 | 11/1978 | Hartog et al. | 564/343 |
| 4,144,317 | 3/1979 | Higuchi et al. | 424/449 |
| 4,201,211 | 5/1980 | Chandrasekaran et al. | 128/268 |
| 4,286,592 | 9/1981 | Chandrasekaran et al. | 128/260 |
| 4,379,454 | 4/1983 | Campbell et al. | 604/897 |
| 4,425,337 | 1/1984 | Alexander et al. | 514/193 |
| 4,440,740 | 4/1984 | Fix et al. | 424/9 |
| 4,562,075 | 12/1985 | Rajadhyaksha | 514/788 |
| 4,573,995 | 3/1986 | Chen et al. | 604/896 |
| 4,588,580 | 5/1986 | Gale et al. | 604/304 |
| 4,597,961 | 7/1986 | Etscorn | 424/28 |
| 4,623,346 | 11/1986 | Von Bittera et al. | 604/896 |
| 4,643,856 | 2/1987 | Nichols | 264/41 |
| 4,647,580 | 3/1987 | Roszkowski | 514/464 |
| 4,704,282 | 11/1987 | Campbell et al. | 424/449 |
| 4,736,710 | 7/1988 | Bondi et al. | 424/449 |
| 4,758,434 | 7/1988 | Kydonieus et al. | 119/82 |
| 4,769,028 | 9/1988 | Hoffmann et al. | 424/447 X |
| 4,797,284 | 1/1989 | Lofer et al. | 424/449 |
| 4,839,174 | 10/1989 | Baker et al. | 424/447 |
| 4,908,027 | 3/1990 | Enscore et al. | 604/890 |
| 4,946,853 | 8/1990 | Bannon et al. | 514/343 |
| 5,016,652 | 5/1991 | Rose et al. | 131/270 |

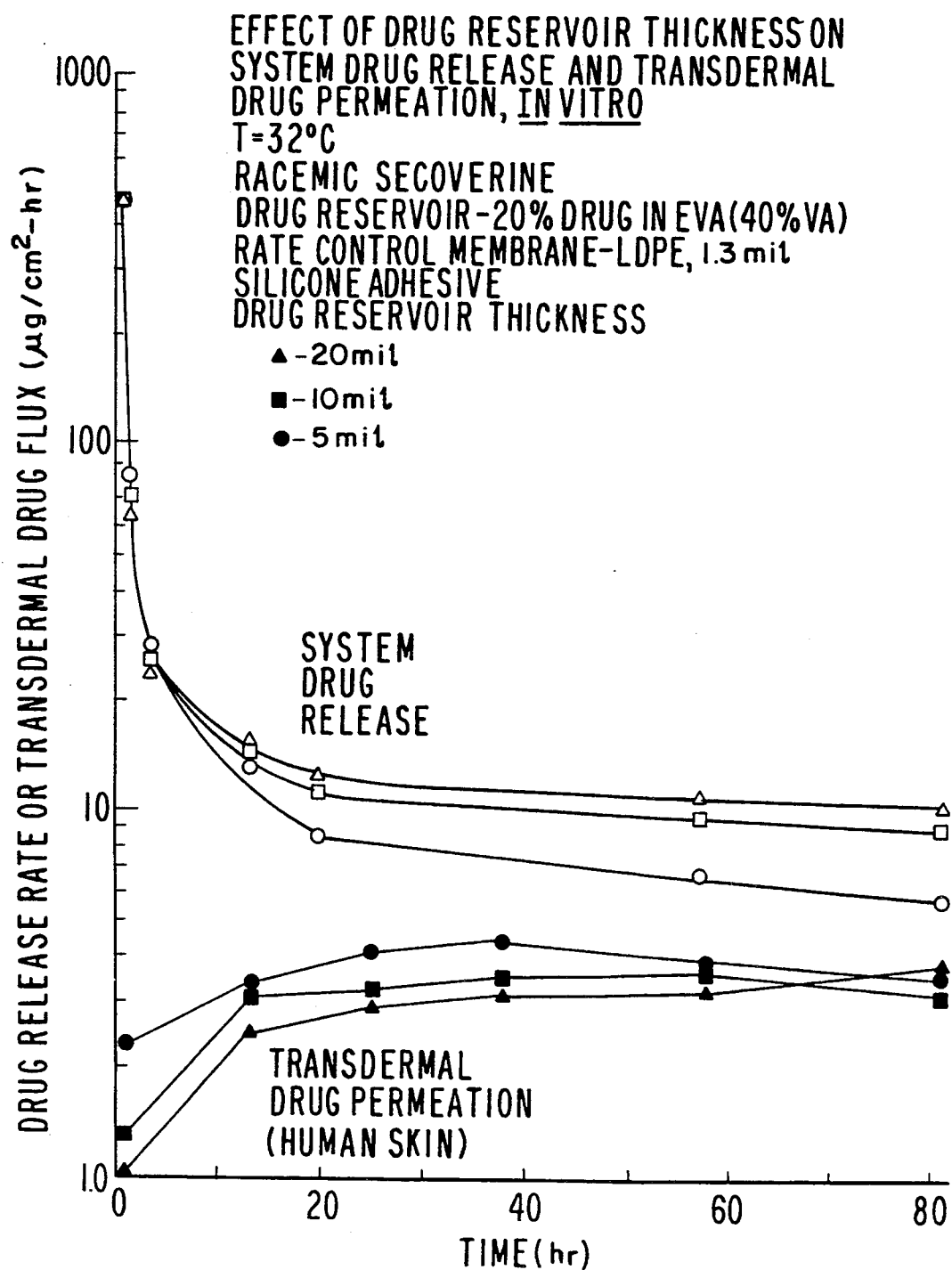

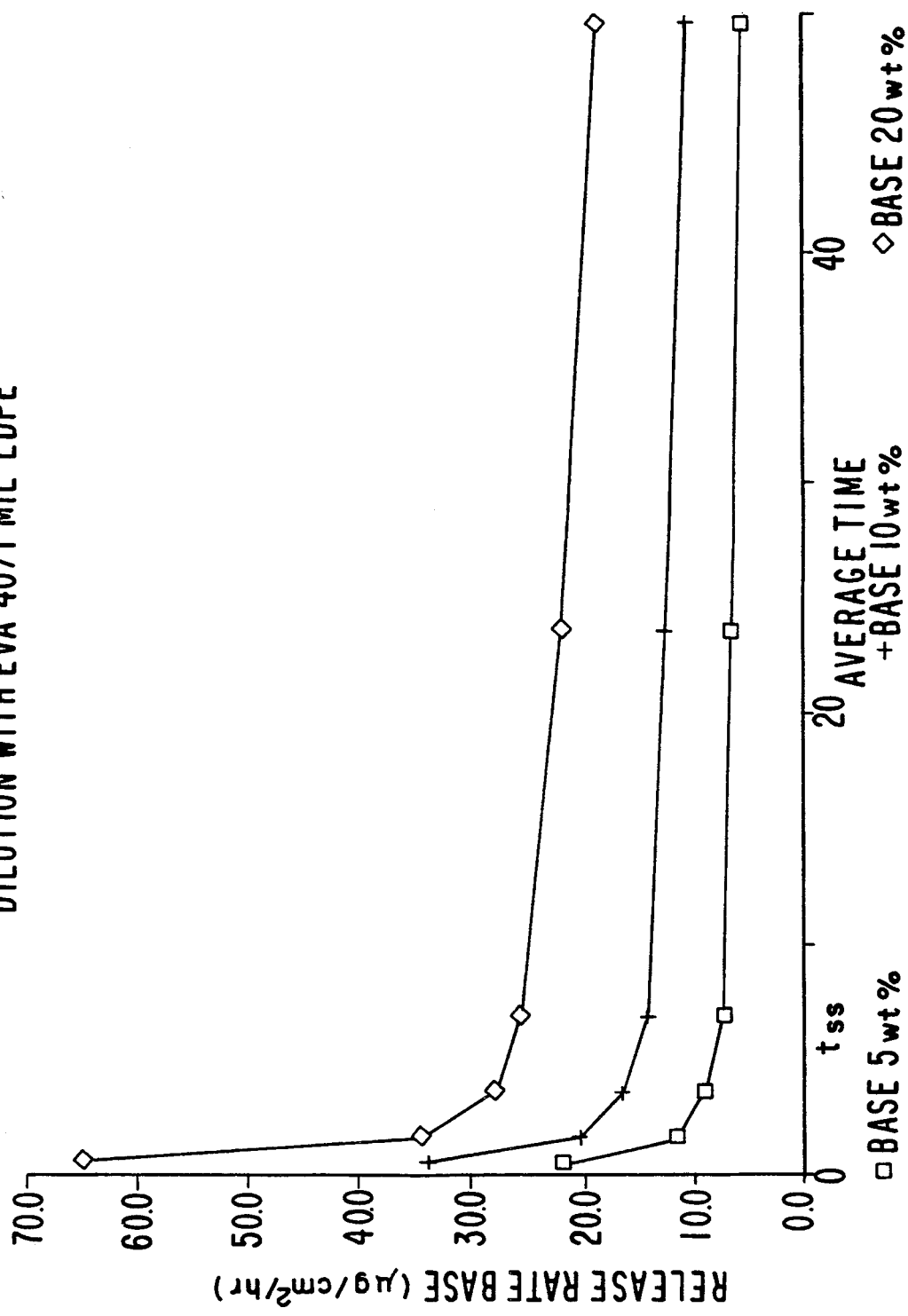

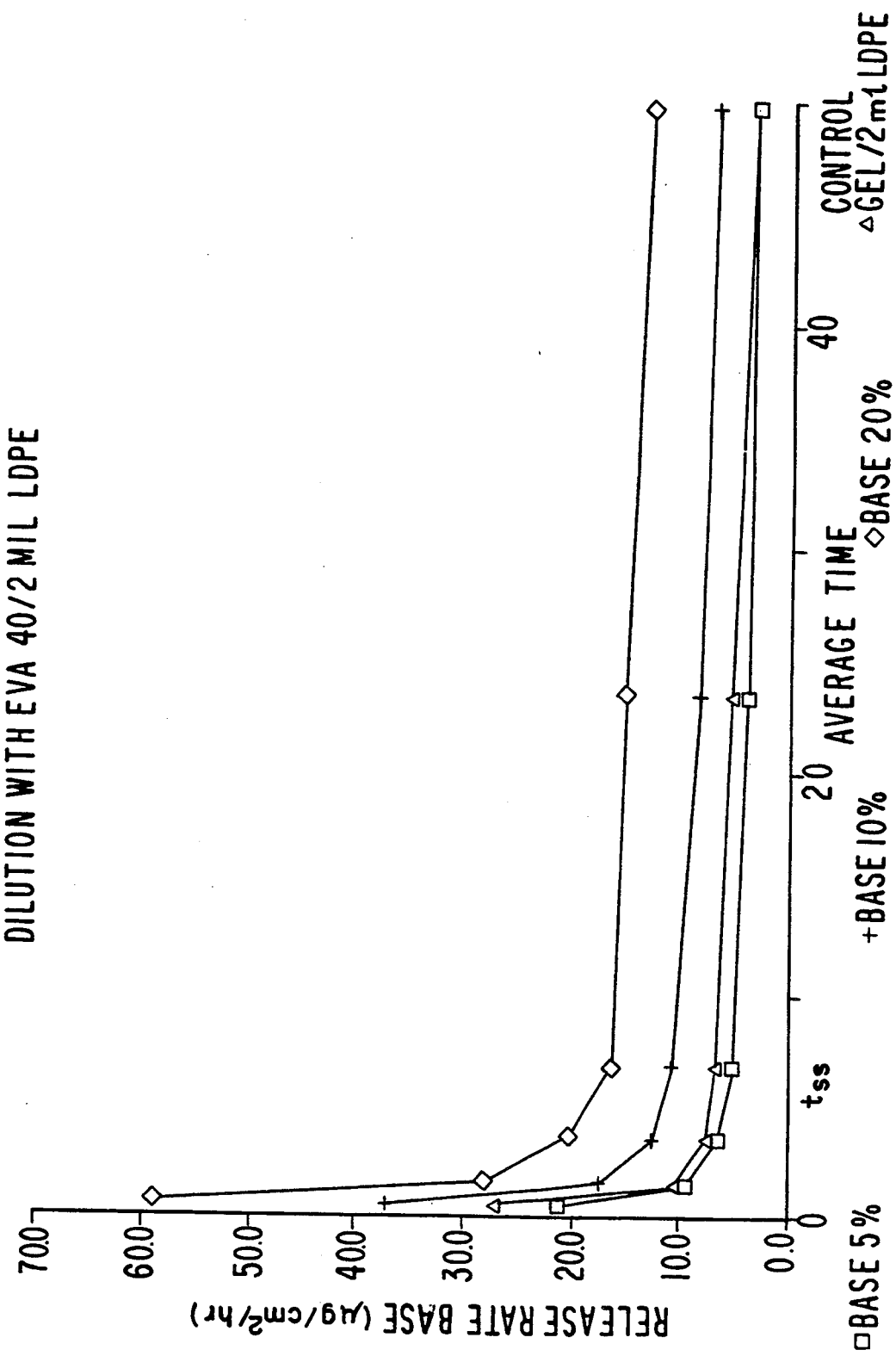

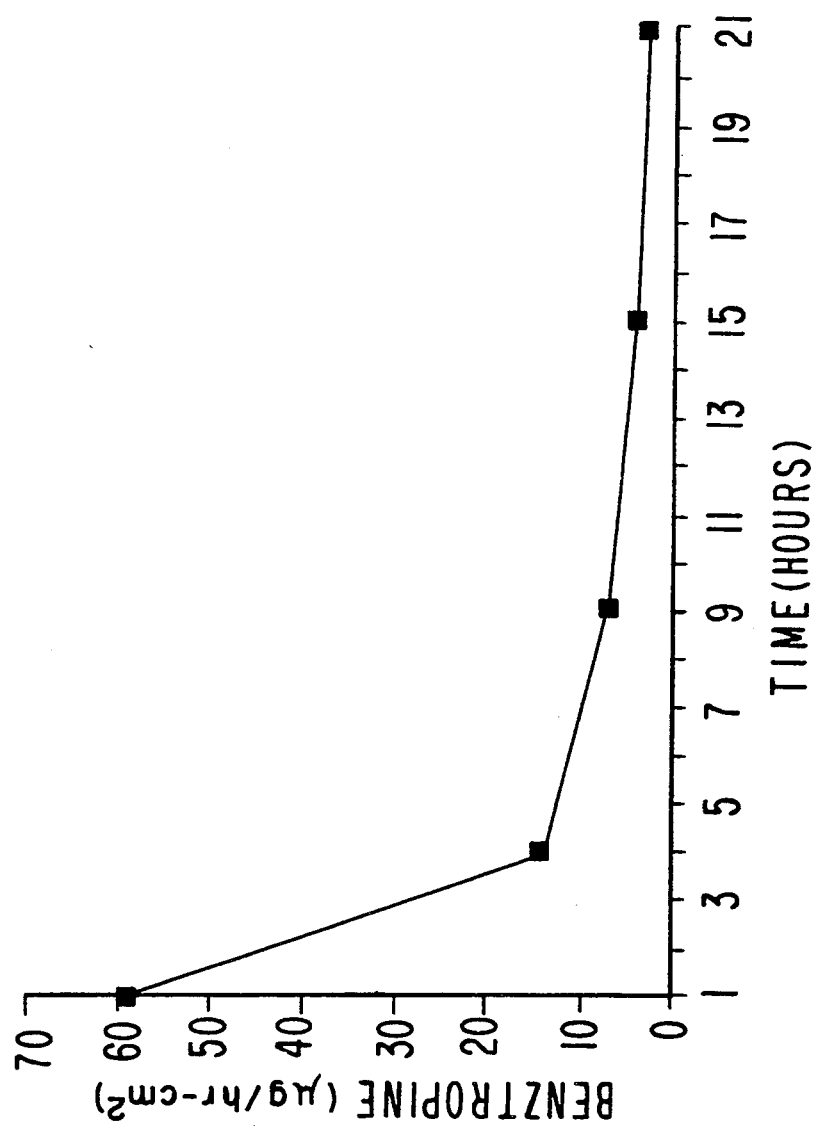

SUBSATURATED TRANSDERMAL THERAPEUTIC SYSTEM HAVING IMPROVED RELEASE CHARACTERISTICS

RELATED PATENT APPLICATIONS

This application is a continuation of our copending, coassigned U.S. patent application Ser. No. 07/284,283 which was is a continuation-in-part of our copending, coassigned U.S. patent application Ser. No. 06/906,730 filed Sep. 12, 1986 for Subsaturated Transdermal Therapeutic System Having Improved Release Characteristics, now U.S. Pat. No. 4,908,027 and the benefit of the filing date of said earlier filed application is claimed under 35 USC §120, now U.S. Pat. No. 4,908,027. It is also related to U.S. patent application Ser. No. 07/206,546 filed Jun. 14, 1988, now abandoned for Subsaturated Nicotine Transdermal Therapeutic System Having Improved Release Characteristics.

FIELD OF THE INVENTION

This invention relates to medical devices in the form of transdermal delivery devices intended to deliver biologically active agents through skin at substantially constant rates for extended periods of time and more particularly to such systems which utilize rate controlling membranes and in-line adhesives.

BACKGROUND OF THE INVENTION

Transdermal delivery devices for the delivery of a wide variety of biologically active agents have been known for some time and representative systems which utilize rate controlling membranes and in-line adhesives are disclosed in U.S. Pat. Nos. 3,598,122, 3,598,123, 3,742,951, 4,031,894, 4,060,084, 4,144,317, 4,201,211 and 4,379,454 which are incorporated herein by reference. Such devices generally comprise an impermeable backing, a drug or active agent reservoir, a rate controlling membrane and a contact adhesive layer which can be laminated or heat sealed together to produce a transdermal delivery device. Although subsaturated systems are known, see U.S. Pat. No. 4,379,454, for example, it is generally desirable that the agent reservoir comprise the agent to be delivered in a suitable carrier at a concentration above the saturation concentration in the carrier. This is done to maintain a unit activity source of the agent so that the delivery rate of the agent will remain substantially constant over the intended administration period; the amount of agent originally present over saturation being the depot or reservoir for the dose of agent ultimately delivered. If the concentration of the agent drops below unit activity during the delivery period, the rate of agent delivery will exhibit a corresponding decrease. It is also generally desirable to minimize the residual agent in the device after use and to accomplish this devices normally utilize, as a carrier, a material which has limited solubility for the agent to be delivered. Although such typical devices have been found useful for the delivery of a wide variety of agents, we have encountered significant problems in producing devices intended to deliver an agent which is capable of dissolving or plasticizing medically acceptable contact adhesives. Such agents are usually, but not always, oily, nonpolar materials, liquid at ambient temperatures, and are either solvents for medically acceptable contact adhesives or are highly soluble therein and cause such adhesives to loose their adhesiveness. In the latter case, the agent may not actually solvate the adhesive but instead plasticize the adhesive and cause it to swell, loose its cohesiveness and adhesiveness, and degrade its other physical properties. As used herein, an agent is a "solvent" for medically acceptable adhesives, and such adhesives are "soluble" in such agents if the agent either dissolves or plasticizes such adhesives as described above.

Agents which are such solvents may be drugs, permeation enhancers or other transdermally deliverable substances. Representative of such agents are drugs such as benztropine base, an anticholinergic useful in the treatment of Parkinsonism, the antispasmolytic drugs, secoverine and dexsecoverine, nicotine, useful in the withdrawal from smoking, and arecoline, a cholinergic and anthelminitic agent, and permeation enhancers such as polyethylene glycol monolaurate, glycerol monolaurate and glycerol monooleate. Ethanol, which is not an oily, nonpolar liquid, is an example of a permeation enhancer which, in high concentrations, can plasticize certain medically acceptable contact adhesives.

Regardless of the initial concentration of the agent in the reservoir and adhesive layers, the devices will equilibrate upon standing. Thus, if the agent is a solvent for the adhesive layer, we have found that substantial quantities migrate from the reservoir through the rate controlling membrane and into the adhesive layer prior to use. The migration will continue until the thermodynamic activity of the agent in the adhesive equals the activity of the agent in the reservoir. Thus, a substantial amount of agent can migrate into the adhesive layer and will be released onto the skin in an uncontrolled manner before the rate controlling membrane can exert any effect on the agent remaining in the reservoir. Also, high concentrations of agent in the adhesive layer and in direct contact with the skin may cause irritation or produce undesirably high plasma levels during the initial period after application to the skin and prior to depletion of the initial loading of agent in the contact adhesive layer. In addition to the deleterious effects on a patient that may be caused by high concentrations of agent in the adhesive, certain adhesives tend to loose their adhesive properties when they are dissolved or plasticized by the agent being delivered.

According to our invention, we have provided a rate controlled, subsaturated transdermal delivery device having an in-line adhesive which delivers an agent which is a solvent for the in-line adhesive and which exhibits improved release characteristics. In certain embodiments of our invention a substantially constant release rate over a substantial portion of a predetermined administration period can be obtained. The device utilizes a subsaturated reservoir containing a sufficient amount of agent to prevent the activity from decreasing by more than about 50% and preferably less than about 25% during the predetermined delivery period. The device is also typically designed such that no more than, and preferably substantially less than, half of the total agent loading in the device is in the adhesive and rate controlling membrane layers after equilibration and prior to use.

Preferred embodiments of our invention are rate controlled drug delivery devices having in-line adhesives for the controlled delivery of the anticholinergic, benztropine, and the tertiary amine secoverine, 1-cyclohexyl-4-C[ethyl(p-methoxy-alpha-methyl phenylethyl)amino]-butazone, an anti-spasmodic agent described in U.S. Pat. Nos. 3,996,245 and 4,125,623 which are incorporated herein by reference. The active, (d) isomer of secoverine is hereinafter referred to as "dexsecoverine". Attempts to produce transdermal delivery devices for these agents by following the aforementioned teachings of the prior art were unsuccessful based on a combination of the above considerations. It is also expected that similar problems will be encountered with respect to other agents which are solvents for medical adhesives.

It is accordingly an object of this invention to provide a rate controlled transdermal delivery device having an in-line adhesive and a subsaturated agent reservoir, which device exhibits improved delivery rate characteristics.

It is another object of this invention to provide a transdermal delivery device for the delivery of agents which are solvents or plasticizers for in-line adhesives.

It is another object of this invention to improve the delivery characteristics of a rate controlled, transdermal delivery device utilizing a subsaturated agent reservoir.

BRIEF DESCRIPTION OF THE DRAWINGS

These and other objects of the invention will be readily apparent from the following description with reference to the accompanying drawings wherein:

FIG. 3 contains plots of in vitro release rates at 32° C. directly into an infinite sink vs. time and through human cadaver skin into an infinite sink vs. time of an embodiment of this invention.

FIGS. 4, 5 and 6 are plots of in vitro delivery rates at 32° C. vs. times of embodiments of this invention.

DESCRIPTION OF THE INVENTION

Figure 1:
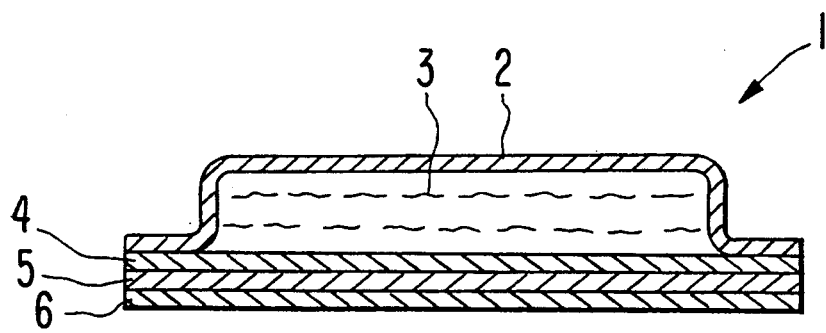
FIG. 1 is a cross section through an embodiment of the transdermal delivery devices according to this invention.
Figure 2:
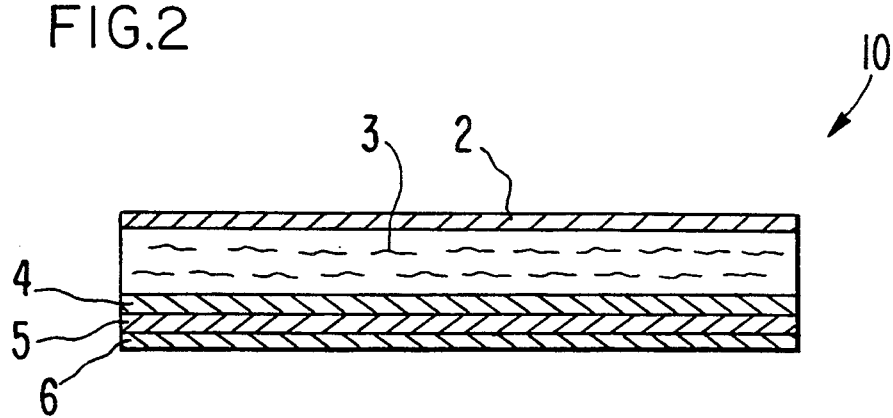
FIG. 2 is a cross section through another embodiment of a transdermal delivery device according to this invention.

Referring now to FIGS. 1 and 2 (like reference numerals referring to common elements), transdermal delivery devices I and 10 according to this invention are shown. Devices 1 and 10 are formed of an impermeable backing 2, an agent reservoir 3, an agent release rate controlling membrane 4, a contact adhesive 5 permeable to the agent, and a strippable release liner 6 adapted to be removed from the adhesive layer prior to application to the skin of the subject to whom the agent is to be administered. As noted above, the agent to be delivered is a solvent for the adhesive forming the adhesive layer 5. In this regard, the reservoir may contain more than one agent according to this invention provided that at least one of the agents is a solvent for the adhesive. Typically, one of the agents could be a drug and another agent could be a permeation enhancer or another drug, for example.

The embodiments of FIGS. 1 and 2 differ in that the agent reservoir 3 of the embodiment of FIG. 1 is less viscous than the reservoir 3 of FIG. 2 such that the impermeable backing 2 is bonded at its periphery to the rate controlling membrane 4 to form a pouch fully enclosing reservoir 3 to prevent it from flowing or oozing. In the embodiment of FIG. 2 the reservoir 3 has sufficient viscosity to maintain its structural integrity without a peripheral or circumferential seal. Although FIGS. 1 and 2 relate to laminated devices, other arrangements of the adhesive, reservoir and rate controlling membranes are usable and include, for example, an adhesive having microcapsules of the agent within a rate controlling membrane dispersed therethrough as shown in aforementioned U.S. Pat. No. 3,598,123.

According to this invention, transdermal delivery devices 1 and 10 are intended to be applied to a patient for a predetermined administration period, typically from about 1-7 days. During the administration period it would be desirable to control the amount of agent that is released from the device so that the agent can be administered to the patient in a predetermined and controlled manner. The in vitro agent release rate or flux from a transdermal delivery device directly into an infinite sink as a function of time can be considered to consist of two phases, a first, initial "transient" phase, and a second, subsequent "steady-state" delivery phase. During the initial transient phase, the agent is released at a high rate as a result of the initial loading of the agent in the adhesive and rate controlling adhesive layers 5 and 4, respectively. This initial pulse release decreases relatively rapidly as a function of $t^{-\frac{1}{2}}$ until the initial loading of agent in the adhesive layer is depleted and the "steady-state" phase in which agent is being delivered from reservoir 3 commences.

$T_{ss}$ shown in FIGS. 4 and 5 represents the time at which the initial transient phase ends and the steady state delivery phase commences. The variation of release rate with time during the steady-state phase depends on the structure of the device. Simple monoliths of the prior art exhibit a theoretical variation of release rate as a function of $t^{-\frac{1}{2}}$ whereas prior art devices having unit activity reservoirs and release rate-controlling membranes exhibit theoretical release rates that vary with $t^0$, i.e., they remain constant Devices according to this invention exhibit a theoretical release rate which varies as a function of $t^n$ where $-\frac{1}{2} \leq n \leq 0$ and preferred embodiments exhibit in vitro release rates which approach those obtained from zero order devices.

According to preferred embodiments of this invention, the steady-state in vitro release rate can be maintained substantially constant from the termination of the initial transient phase until the expiration of the predetermined administration period. As used herein, the in vitro agent delivery rate is considered to be "substantially constant" if the steady-state rate does not vary more than about ±50%, and preferably no more than ±15%, during the steady state administration period.

As used herein, the term "agent" is used in its broadest sense to mean any material which is to be delivered into the body of a human or animal to produce a beneficial, therapeutic or other intended effect, such as permeation enhancement, for example, and is not limited to drugs and pharmaceutical products. The maximum allowable concentration of the agent in the adhesive will be determined by such factors as the agent concentration at which the adhesive properties are impaired, the agent concentration at which irritation problems or unacceptably high initial transdermal agent fluxes, for example, are observed. When such undesirable effects occur, it is necessary that the initial activity of the agent in the adhesive be at a lower level. Because the device will equilibrate on standing, the activity (but not necessarily the concentration) of the agent in the reservoir will ultimately be the same as the activity of the agent in the adhesive layer.

Transdermal delivery devices, according to our invention, have the following characteristics:

1. The device utilizes an in-line adhesive to maintain the device on the skin;

2. The agent to be delivered is a solvent for the in-line adhesive;

3. The initial equilibrated concentration of the agent in the reservoir 3 and the adhesive 5 is below saturation, expressed alternatively, the activity is less than 1.0;

4. The reservoir 3 comprises the agent dissolved in a solvent with respect to which rate controlling membrane 4 is substantially impermeable;

5. In preferred embodiments the initial loading of the agent in reservoir 3 is sufficient to prevent the activity of the agent in the reservoir from decreasing by more than about 75% and preferably no more than about 25% during the predetermined period of administration; and 6. In preferred embodiments the thicknesses of the adhesive, rate controlling membrane and reservoir layers are selected so that at least 50% and preferably at least 75% of the initial equilibrated agent loading is in the reservoir layer.

To design a system according to our invention, the permeability of skin to the agent to be delivered, the amount of agent required to saturate the agent binding sites in the skin, the maximum activity of agent in the adhesive layer that can be tolerated without loss of adhesive properties and without producing undesirable initial drug pulses, skin irritation or undesirable sensations would be determined by suitable in vitro and in vivo tests. Having determined the maximum allowable activity of agent in the adhesive; a somewhat lower initial activity would typically be employed to provide for a factor of safety. In some instances, such as in the initial administration of the agent or where intermittent, as opposed to continuous, delivery periods are prescribed, the initial loading of agent in the adhesive layer 5 and rate controlling membrane 4 may correspond approximately to the amount of agent needed to saturate the agent binding sites in the skin below the delivery device.

In preferred embodiments the equilibrated agent loading in the reservoir layer 3 is selected to be sufficient to enable the total dose of agent delivered during the predetermined administration period to be delivered while maintaining the decrease in activity of the agent in the non-permeating solvent forming reservoir 3 within the limits noted above. The total loading of agent in each layer of the device can be readily varied without changing the activity simply by increasing or decreasing the thickness of the adhesive layer 5 and/or reservoir layer 3, and also by appropriate selection of the total surface area of the device through which agent is delivered. Because the rate controlling membrane can only act as a release rate limiting element on agent which is in the reservoir; the reservoir thickness should be selected, with respect to the thicknesses of the rate controlling membrane and the adhesive layers, such that at least half, and preferably substantially more, of the initial equilibrated agent loading is in the reservoir.

The rate-controlling membrane 4 would be selected such that the flux of the agent through the membrane into an infinite sink is preferably no greater than the in vitro flux of the agent through skin (which would produce about 50% device control) and preferably substantially less. If the skin flux is greater than the membrane flux by a factor of about 2.4, for example, approximately 70% of the rate control is obtained from the device.

Suitable materials from which the various layers of the device according to this invention can be made are known to the art and many are described in the aforementioned U.S. patents.

Having thus generally described our invention, the following description and examples will illustrate how variations of the above described parameters affect the administration of the agent.

Secoverine normally exists as a racemic mixture of d- and l-isomers, the d-isomer, dexsecoverine, being the biologically active ingredient. We have determined that dexsecoverine diffuses through normal skin at substantially the same rate as the racemic mixture and, therefore, if dexsecoverine is used as the agent in the reservoir 3 the agent flux through the skin need be only about one half that which would otherwise be required if secoverine were delivered.

EXAMPLE 1

Transdermal delivery devices for the controlled delivery of dexsecoverine were prepared utilizing Dow Corning DC 355 silicone adhesive as the highly permeable medical adhesive, low density polyethylene {LDPE}or ethylene vinylacetate (EVA) copolymer (9% VA) as the rate controlling membrane, EVA (40% VA) as the non-diffusible drug reservoir diluent, pigmented medium density polyethylene/aluminized polyester as the impermeable backing member and racemic secoverine or dexsecoverine as the source of dexsecoverine. Secoverine and dexsecoverine are extremely soluble (essentially miscible) in the EVA (40% VA) diluent and thus the weight percent concentration in the diluent corresponds approximately to the thermodynamic activity. Secoverine and dexsecoverine are solvents for DC355 and form solutions therewith at concentrations of at least 300 mg/cm$^3$ and adverse effects were observed when the concentration reached about 50 mg/cm$^3$. Thus according to the preferred dexsecoverine delivering embodiments of this invention, it is desirable to maintain the agent concentration in the adhesive below about 45 mg/cm$^3$ which corresponds to an activity of about 0.15 in the drug reservoir and the adhesive layers. The thicknesses of the adhesive and rate controlling layers in the subsaturated system were selected to provide an initial pulse of about 225 μg/cm$^2$ to saturate the agent binding sites in the skin, the contribution to the pulse of each such layer being dependent on the thickness of the layer and the solubility of the agent in each layer. A thicker layer would provide a higher initial pulse and a thinner layer would provide a smaller initial pulse for the same initial activity. One or 1.3 mil LDPE and 2 or 4 mil EVA (9% VA) rate control membranes were utilized in the preferred embodiments, and drug reservoirs of approximately 5–20 mils were tested. A 5 mil thickness was sufficient to prevent the activity of the agent in the reservoir 3 from decreasing by more than 30% during a four-day administration period. The in vitro release rates of various subsaturated dexsecoverine systems are compared to the characteristics for unit activity systems in Table I. FIG. 3 shows the in vitro release rates at 32° C. directly into an infinite sink and through cadaver skin into an infinite sink from racemic secoverine systems and illustrates the effect of varying reservoir thicknesses on in vitro release rates.

TABLE I

| Drug Source | Unit Activity System Dexsecoverine | Subsaturated Systems Dexsecoverine | | | Secoverine | | |
|---|---|---|---|---|---|---|---|
| Drug Activity | 1.00 | 0.06 | 0.15 | 0.10 | 0.20 | 0.20 | 0.20 |
| Drug Concentration (mg/cm$^3$ in reservoir) | — | — | — | — | — | — | — |
| Membrane | LDPE | EVA (9% VA) | LDPE | EVA (9% VA) | LDPE | LDPE | LDPE |
| Membrane Thickness (mils) | 1.0 | 4.0 | 1.0 | 2.0 | 1.3 | 1.3 | 1.3 |
| Adhesive Thickness (mils) | 1.7 | 1.8 | 1.7 | 1.4 | 1.7 | 1.7 | 1.7 |
| Reservoir Thickness (mils) | 5 | 5.0 | 5.0 | 5.0 | 20.0 | 10.0 | 5.0 |
| Initial Burst ($\mu$g/cm$^2$): | | | | | | | |
| from membrane | 170 | 142 | 26 | 118 | | | |
| from adhesive | 1325 | 84 | 199 | 109 | | | |
| Total | 1495 | 226 | 225 | 227 | | | |
| Avg. Steady State In vitro Releae Rate at 32° C. ($\mu$g/cm$^2$/hr) | 57 | 6.5 | 8.5 | 22 | | | |
| Range (over 24–96 hr) | 60–54 | 7.5–5.5 | 10–7 | 24–18 | | | |

We have determined that to achieve anti-spasmodic activity from the continuous transdermal administration of secoverine, approximately 1 to 10 nanograms/ml of dexsecoverine should be maintained in the plasma. We have also discovered that the permeability of average human skin when exposed to unit activity sources of either secoverine or dexsecoverine appears to be in the range of approximately 20 to 60 $\mu$g/cm$^2$/hr. In order to deliver adequate amounts of a drug from a reasonably sized system, a target steady-state in viva delivery rate of dexsecoverine from 10–40 $\mu$g/hr was selected which rate can be readily achieved according to our invention in a rate controlled device of reasonable size of from about 5 to 60 cm$^2$. Delivery periods of about 3–5 days can be obtained from subsaturated devices of Table 1, and administration periods up to about 7 days can be attained by increasing the thickness of the reservoir to about 10 mils.

EXAMPLE 2

Subsaturated transdermal delivery devices similar to those of Example I, but intended to deliver benztropine, base are fabricated having an agent reservoir diluent of EVA (40% VA), and a 1 mil LDPE rate controlling membrane. Benztropine base is soluble to about 650 mg/g of EVA (40% VA). 2.5 cm$^2$ devices are fabricated using a highly permeable, amine-resistant silicone adhesive available from Dow Corning, (X7-2920) or polyisobutylene/mineral oil adhesives, an impermeable backing, and an 8 mil thick reservoir layer having an initial benztropine loading of 5, 10, and 20 weight percent equivalent to activities of 0.125, 0.25, and 0.5. The in vitro release rates to be obtained from such devices, using 1 mil LDPE rate-controlling membranes, are shown in FIG. 4. The effect of using a 2-mil LDPE rate controlling membrane is shown in FIG. 5.

The permeability of average skin to benztropine is in the range of 70 to 90 $\mu$g/cm$^2$/hr, and systems as described above can deliver benztropine in vivo at therapeutically useful rates of 10 to 40 $\mu$g/hr. The size of the device can be selected to provide daily doses of about 0.4 to 4.5 mg for up to 4 days.

EXAMPLE 3

Benztropine transdermal delivery devices for use in clinical testing were fabricated as set forth generally in Example 2 from a 10% benztropine in 90% EVA 40 reservoir composition into 5 cm$^2$ patches using 1.5 mil LDPE rate controlling membranes and 1.8 mil amine resistant adhesive layers. With a 5 mil reservoir layer the devices contained about 6.4 mg of benztropine and are intended for a 24 hour administration period. The in vitro release rate at 35° C. into a infinite sink is shown in FIG. 6. When applied to human subjects on a daily basis, anticholinergically effective transdermal delivery of benztropine can be obtained.

Having thus generally described our invention and preferred embodiments thereof, it is apparent that various modifications and substitutions will be apparent to workers skilled in the art, which can be made without departing from the scope of our invention which is limited only by the following claims wherein:

We claim:

1. A medical device utilizing an in-line adhesive for the transdermal administration of an agent that is a solvent for said adhesive, said device being adapted to deliver said agent throughout a predetermined administration period said device comprising, in combination:
   a) an agent reservoir comprising said agent dissolved in a solvent at a concentration less than saturation and at an initial equilibrated agent loading sufficient to prevent the activity of said agent in said solvent from decreasing by more than 75% during said administration period;
   b) agent release rate controlling means disposed in the path of agent migration from said reservoir to the skin, said rate controlling means being permeable to said agent and substantially impermeable to said solvent; and
   c) adhesive means disposed in the path of agent migration from said release rate controlling means to the skin, said adhesive being soluble in said agent the initial equilibrated concentration of said agent in said reservoir being at a level at which the adhesive maintains adhesive properties.

2. The device of claim 1 wherein at least 50% of the initial loading of the agent in the device is in the agent reservoir.

3. The device of claim 1 wherein said decrease in activity is no greater than 25%.

4. The device of claim 1 wherein at least 75% of the initial agent loading is in the reservoir.

5. The device of claim 1 wherein said agent is an oily, non-polar material, liquid at body temperature.

6. The device of claim 1 wherein said reservoir contains more than one agent at least one of which is an oily, nonpolar material, liquid at body temperature.

7. The device of claim 1 wherein said agent solubilizes said adhesive.

8. The device of claim 1 wherein said agent plasticizes said adhesive.

9. The device of claim 1 wherein the activity of the agent in the reservoir is no greater than 0.50.

10. The device of claim 2 wherein the activity of the agent in the reservoir is no greater than 0.50.

11. The device of claim 3 wherein the activity of the agent in the reservoir is no greater than 0.50.

12. The device of claim 4 wherein the activity of the agent in the reservoir is no greater than 0.50.

13. The device of claim 1 wherein the activity of the agent in the reservoir is no greater than 0.25.

14. The device of claim 2 wherein the activity of the agent in the reservoir is no greater than 0.25.

15. The device of claim 3 wherein the activity of the agent in the reservoir is no greater than 0.25.

* * * * *